(12) United States Patent
Shen et al.

(10) Patent No.: US 9,101,030 B2
(45) Date of Patent: Aug. 4, 2015

(54) LED LIGHTING DEVICE, SYSTEM, AND METHOD WITH AIR QUALITY DETECTION

(71) Applicant: ZHEJIANG SHENGHUI LIGHTING CO., LTD, Jiaxing (CN)

(72) Inventors: Jinxiang Shen, Jiaxing (CN); Chaoqun Sun, Jiaxing (CN); Xia Wang, Jiaxing (CN)

(73) Assignee: ZHEJIANG SHENGHUI LIGHTING CO., LTD, Jiaxing (CN)

( * ) Notice: Subject to any disclaimer, the term of this patent is extended or adjusted under 35 U.S.C. 154(b) by 0 days.

(21) Appl. No.: 14/296,566

(22) Filed: Jun. 5, 2014

(65) Prior Publication Data

US 2014/0285114 A1    Sep. 25, 2014

Related U.S. Application Data

(63) Continuation-in-part of application No. PCT/CN2013/076561, filed on May 31, 2013.

(30) Foreign Application Priority Data

Mar. 15, 2013  (CN) .......................... 2013 1 0085107

(51) Int. Cl.
| | |
|---|---|
| F21V 23/04 | (2006.01) |
| H05B 33/08 | (2006.01) |
| G01N 33/00 | (2006.01) |
| H05B 37/02 | (2006.01) |
| F24F 11/00 | (2006.01) |

(52) U.S. Cl.
CPC ........ *H05B 33/0884* (2013.01); *G01N 33/0063* (2013.01); *H05B 37/0272* (2013.01); *F24F 11/0017* (2013.01); *Y02B 30/78* (2013.01)

(58) Field of Classification Search
None
See application file for complete search history.

(56) References Cited

U.S. PATENT DOCUMENTS

| | | | |
|---|---|---|---|
| 2009/0267540 A1* | 10/2009 | Chemel et al. ................. | 315/297 |
| 2010/0094142 A1* | 4/2010 | Yu et al. ......................... | 600/485 |
| 2010/0204841 A1* | 8/2010 | Chemel et al. ................. | 700/282 |
| 2013/0038470 A1* | 2/2013 | Niemeyer et al. ........ | 340/870.11 |

FOREIGN PATENT DOCUMENTS

DE       202005016341 U1 *  2/2006

* cited by examiner

*Primary Examiner* — Douglas W Owens
*Assistant Examiner* — Dedei K Hammond
(74) *Attorney, Agent, or Firm* — Anova Law Group, PLLC

(57) ABSTRACT

LED lighting devices/systems having air quality detection functions and methods for detecting air quality using the LED lighting devices/systems are provided. Exemplary LED lighting device includes an air quality detection unit configured to detect air quality parameter; a controller unit connected to the air quality detection unit to process data corresponding to the air quality parameter; an LED light source assembly controlled by the controller unit and configured to provide lighting; and an LED driver and power supply unit connected to drive the LED light source assembly, and to supply power to the entire LED lighting device. Exemplary LED lighting system includes at least two nodes each including an LED lighting device. By combining an air quality detection unit with an LED lighting device that are widely distributed and installed, the disclosed LED lighting devices/systems thus provide real-time and convenient air quality monitoring.

16 Claims, 5 Drawing Sheets

LED LIGHTING DEVICE, SYSTEM, AND METHOD WITH AIR QUALITY DETECTION

CROSS-REFERENCES TO RELATED APPLICATIONS

This application is a continuation in part of PCT Application No. PCT/CN PCT/CN2013/076561, filed on May 31, 2013, which claims the priority to Chinese Patent Application No. 201310085107.6, filed on Mar. 15, 2013, the entire contents of which are incorporated herein by reference.

FIELD OF THE DISCLOSURE

The present disclosure relates to the field of LED (light emitting diode) lighting technology and, more particularly, relates to LED lighting devices/systems having air quality detection functions, and methods for detecting air quality using the LED lighting devices/systems.

BACKGROUND

LED devices have been widely used in various lighting areas (e.g., for a low-carbon lifestyle) and may provide advantages including energy conservation, environmental protection, controllable lighting, solid state lighting, and long operational lifetime. As environmental problems become more of a concern, there have been growing emphases and considerations on environmental protection and management. It is therefore desirable to have a device with convenient air pollution monitoring function to facilitate settings of regional environmental standards and to help control/management of industrial and agricultural productions. Existing air quality detection devices are large and relatively expensive. Further, their operations and maintenance often require specialized operators and involve cumbersome processes.

Thus, there is a need to overcome these and other problems of the prior art and to provide LED lighting devices/systems having air quality detection functions, and methods for detecting air quality using the LED lighting devices/systems.

BRIEF SUMMARY OF THE DISCLOSURE

One aspect or embodiment of the present disclosure includes an LED (light emitting diode) lighting device having an air quality detection function. The LED lighting device includes at least one air quality detection unit configured to detect at least one air quality parameter; at least one controller unit connected to the air quality detection unit to process data corresponding to the at least one air quality parameter detected and collected by the at least one air quality detection unit; at least one LED light source assembly controlled by the at least one controller unit and configured to provide lighting; and at least one LED driver and power supply unit connected to the at least one LED light source assembly to drive the at least one LED light source assembly, and to supply power to the entire LED lighting device.

The air quality detection unit includes an analog circuit having an analog sensor, a signal processing circuit, and a signal processing circuit. The analog sensor is configured to convert a non-electrical signal corresponding to the at least one air quality parameter into an analog signal and then to output the analog signal. The signal processing circuit is connected to the analog sensor to scale, filter, and amplify the analog signal from the analog sensor and to further output a processed analog signal. The ADC circuit is configured to receive the processed analog signal from the signal processing circuit, to convert the processed analog signal into a digital signal, and to output the digital signal to the at least one controller unit for conversion, calculation, and storage of the digital signal.

Optionally, the air quality detection unit is a digital sensor directly connected to the at least one controller unit to provide a digital signal corresponding to the at least one air quality parameter. The at least one controller unit is configured to read, convert, calculate, and store the digital signal according to a bus protocol. Optionally, the air quality detection unit includes at least one analog circuit and at least one digital sensor.

The at least one air quality parameter includes concentrations of one or more air components including, for example, carbon monoxide, methanol, ethanol, formaldehyde, isopropanol, acetaldehyde, $SO_2$, $H_2$, $H_2S$, phenol, formaldehyde, ethylene, and PM 2.5 (particulate matter 2.5, e.g., suspended particulates smaller than 2.5 μm in aerodynamic diameter), in the air.

The LED lighting device further includes an LED indication panel unit connected to the at least one controller unit, the LED indication panel unit including a plurality of light emitting diodes with different colors to indicate different air qualities corresponding to the at least one air quality parameter.

The LED lighting device further includes a storage unit connected to the at least one controller unit and configured to support a pluggable SD card. The storage unit is further configured to store the data corresponding to the at least one air quality parameter in real-time according to a setting of a starting date and an ending date.

The LED lighting device further includes a display unit connected to the at least one controller unit and configured to display in real-time an air quality index (AQI) corresponding to the at least one air quality parameter and to display information including the air quality factor for users to query back. The display unit includes LED digital tube, IXD, OLED, or a combination thereof.

The LED light source assembly controlled by the at least one controller unit is further configured as an alarm unit for receiving the data corresponding to the at least one air quality parameter from the at least one controller unit and for providing a flashing warning light.

The LED lighting device further includes a wireless transceiver unit connected to the at least one controller unit and configured to transmit the data corresponding to the at least one air quality parameter to a smart terminal.

The LED lighting device further includes a lamp body such that the at least one air quality detection unit, the at least one controller unit, the at least one LED light source assembly, and the at least one LED driver and power supply unit are integrated together in the lamp body.

Another aspect or embodiment of the present disclosure includes an LED lighting system having an air quality detection function. The LED lighting system includes one or more LED lighting devices and at least one smart terminal. Each of the one or more LED lighting devices includes at least one air quality detection unit configured to detect at least one air quality parameter; at least one controller unit connected to the air quality detection unit to process data corresponding to the at least one air quality parameter detected and collected by the at least one air quality detection unit; at least one LED light source assembly controlled by the at least one controller unit and configured to provide lighting; at least one LED driver and power supply unit connected to the at least one LED light source assembly to drive the at least one LED light source assembly, and to supply power to the entire LED lighting device; and at least one wireless transceiver unit connected to the at least one controller unit and configured to transmit the data corresponding to the at least one air quality parameter to the at least one smart terminal.

The wireless transceiver unit is supported by one or more of zigbee, WiFi, and bluetooth. The smart terminal includes a mobile phone, a tablet PC, a desktop computer, and a notebook.

The LED lighting system includes at least two LED lighting device nodes with each node including one LED lighting device. Each node is configured to transmit a wireless signal corresponding to the at least one air quality parameter from the at least one wireless transceiver unit to other different nodes covered by other wireless signals correspondingly.

Each of the one or more LED lighting devices further includes a lamp body such that the at least one air quality detection unit, the at least one controller unit, the at least one LED light source assembly, the at least one LED driver and power supply unit, and the at least one wireless transceiver unit are integrated together in the lamp body.

Another aspect or embodiment of the present disclosure includes a method for detecting an air quality by providing an LED lighting device including an air quality detection unit, a controller unit, an LED light source assembly, an LED driver and power supply unit, and a wireless transceiver unit. Air quality parameters are detected in real-time to provide a detected value by the air quality detection unit. The air quality detection unit sends the detected value to the controller unit. The detected value of the air quality parameters is obtained by the controller unit. The detected value is sent out to a smart terminal via the wireless transceiver unit. The controller unit compares the detected value of the air quality parameters with a standard threshold value. It is then determined whether the detected value of the air quality parameters is within a predetermined range. When the detected value of the air quality parameters is within the predetermined range, the above described steps are repeated for further detection. When the detected value of the air quality parameters exceeds the predetermined range, the controller unit sends a warning signal to the LED drive and power supply unit such that the LED drive and power supply unit controls the LED light source assembly to provide a flashing warning light.

The LED lighting device further includes a lamp body such that the air quality detection unit, the controller unit, the LED light source assembly, the LED driver and power supply unit, and the wireless transceiver unit are integrated together in the lamp body.

Each of the air quality parameters includes concentrations of one or more of carbon monoxide, methanol, ethanol, formaldehyde, isopropanol, acetaldehyde, $SO_2$, $H_2$, $H_2S$, phenol, formaldehyde, ethylene, and PM 2.5 (particulate matter 2.5), in the air.

Other aspects or embodiments of the present disclosure can be understood by those skilled in the art in light of the description, the claims, and the drawings of the present disclosure.

BRIEF DESCRIPTION OF THE DRAWINGS

The following drawings are merely examples for illustrative purposes according to various disclosed embodiments and are not intended to limit the scope of the present disclosure.

DETAILED DESCRIPTION

Reference will now be made in detail to exemplary embodiments of the disclosure, which are illustrated in the accompanying drawings. Wherever possible, the same reference numbers will be used throughout the drawings to refer to the same or like parts.

LED lighting devices/systems having air quality detection functions, and methods for detecting air quality using the LED lighting devices/systems are provided with low cost, with simple structure, and with a wide application range for various occasions. In addition to providing normal lighting function, the disclosed LED lighting devices/systems having air quality detection functions can provide real-time monitoring of air quality in the region where the LED lighting devices/systems are located.

As such, the disclosed LED lighting device having air quality detection function can include a built-in air quality detection unit to provide a normal lighting function and also to detect air quality of the region. The detected data from the air quality detection unit can be sent to a smart terminal for performing analysis and statistics to provide real-time data (e.g., data over time, data for user inquiry, warning messages, or any related information) of the air quality of the region. In the meanwhile, if the air quality is undesirable or fails to meet certain standard, the disclosed LED lighting device can provide a flashing warning light such that people in the region can be reminded, e.g., without inhaling too much harmful air.

Because the air quality detection unit is built-in within the disclosed LED lighting device, the detected data of the air quality can be collected and handled in real-time such that air quality index (AQI) of surrounding environment can be conveniently and timely monitored. The disclosed LED lighting devices having air quality detection functions can thus be provided with low cost, with simple structure, with ease to install, and with many applications.

Figure 1:
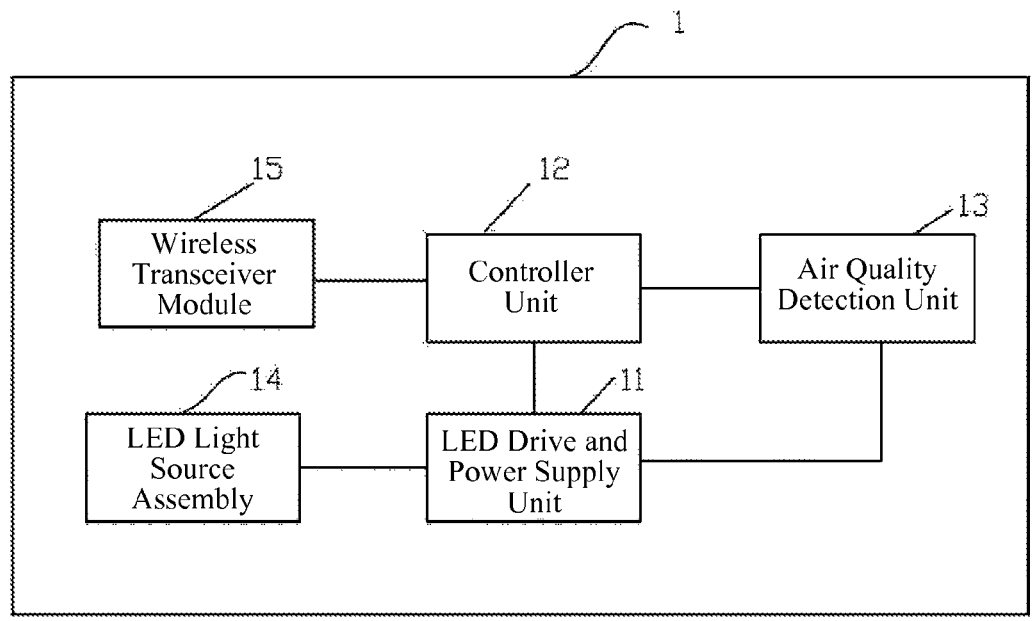
FIG. 1 depicts an exemplary LED lighting device consistent with various disclosed embodiments.

FIG. 1 depicts an exemplary LED lighting device having an air quality detection unit in accordance with various disclosed embodiments. The exemplary LED lighting device 1 includes an LED drive and power supply unit 11, a controller unit 12, an air quality detection unit 13, an LED light source assembly 14, and/or a wireless transceiver unit 15.

The LED drive and power supply unit 11 can be directly connected to the LED light source assembly 14. The LED drive and power supply unit 11 can provide power to the entire LED lighting device 1.

The controller unit 12 can be connected to the air quality detection unit 13. The controller unit 12 can be configured to convert, calculate, store, and/or otherwise process data collected by the air quality detection unit 13.

The wireless transceiver unit 15 can be supported by one or more of zigbee, WiFi, and bluetooth. The wireless transceiver unit 15 and the controller unit 12 can be connected for data transmission there-between.

The LED light source assembly 14 can include one or more LED light sources. The LED light source assembly 14 can provide a normal lighting function. Meanwhile, the controller unit 12 can provide data/information of the detected air quality and can provide flashing warning light when necessary. The flashing warning light can be flashed at a certain frequency and at a time interval.

Figure 2:
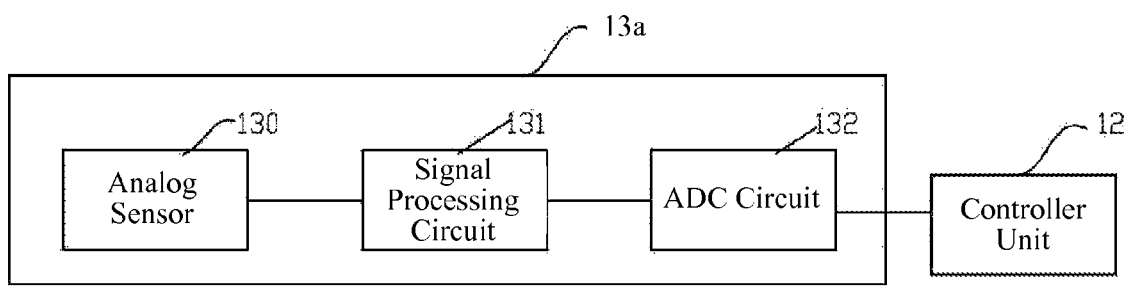
FIG. 2 depicts an exemplary connection of an air quality detection unit with a controller unit in an LED lighting device consistent with various disclosed embodiments.

FIG. 2 depicts an exemplary connection of an air quality detection unit with a controller unit in an LED lighting device consistent with various disclosed embodiments. As shown in FIG. 2, the air quality detection unit 13 can include an analog circuit 13a including an analog sensor 130, a signal processing circuit 131, and/or an ADC circuit 132.

The analog sensor 130 can convert a non-electrical signal of detected air quality parameter(s) into an analog signal. The analog signal can be scaled, filtered, and/or amplified by the signal processing circuit 131, which can then output the processed analog signal to the ADC circuit 132. The ADC circuit 132 can collect the processed analog signal and convert the processed analog signal into a digital signal. The digital signal can be outputted to the controller unit 12 to convert, calculate, store, and/or otherwise process the digital signal to provide collected data corresponding to the air quality parameter(s).

Figure 3:
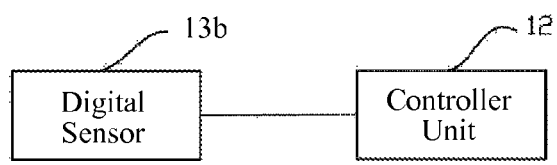
FIG. 3 depicts another exemplary connection of an air quality detection unit with a controller unit in an LED lighting device consistent with various disclosed embodiments.

FIG. 3 depicts another exemplary connection of an air quality detection unit with a controller unit in an LED lighting device consistent with various disclosed embodiments. As shown in FIG. 3, the air quality detection unit in FIGS. 1-2 can be replaced by a digital sensor 13b. The digital sensor 13b can be directly connected to the controller unit 12. The digital sensor 13b can output a digital signal corresponding to air quality parameters to the controller unit 12. The controller unit 12 can control a configuration according to a corresponding bus protocol to read the digital signal corresponding to air quality parameters to perform conversion, calculation, and storage thereof to provide the detected data. The controller unit 12 can be a microcontroller, a digital signal processor, a digital integrated circuit (IC) controller, or a combination thereof.

Figure 4:
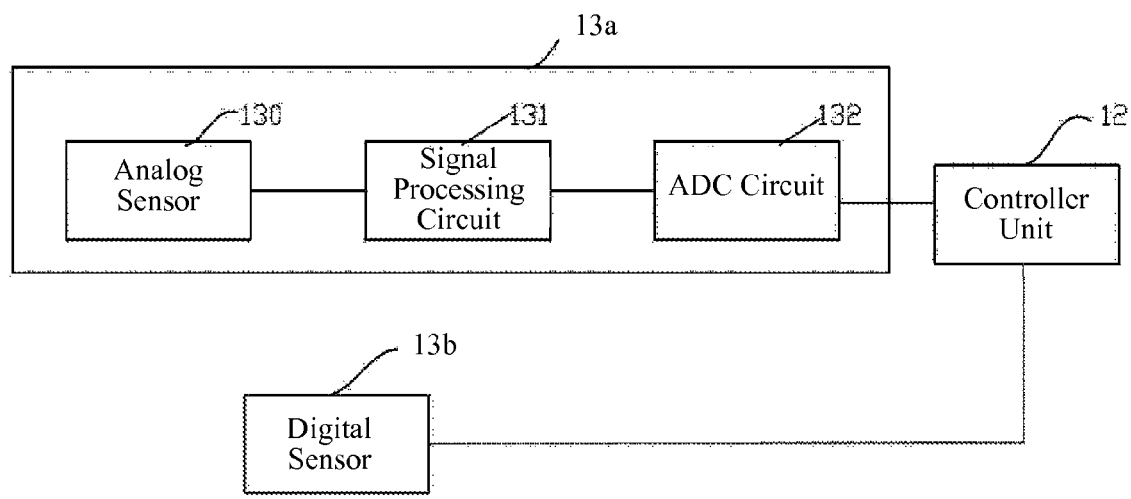
FIG. 4 depicts another exemplary connection of an air quality detection unit with a controller unit in an LED lighting device consistent with various disclosed embodiments.

The two exemplary types of air quality detection units 13a and 13b of FIGS. 2-3 can be configured in a single LED lighting device as shown in FIG. 4. For example, the LED lighting device in FIG. 4 can simultaneously include at least one analog circuit 13a and at least one digital sensor 13b. This configuration can be used for different detections to satisfy different detection needs using a same LED lighting device. Detection accuracy and detection quality can thus be improved and valid detections can be ensured.

The air quality detection units of FIGS. 1-4 can detect concentrations of one or more air components including carbon monoxide, methanol, ethanol, formaldehyde, isopropanol, acetaldehyde, SO2, H2, H2S, phenol, formaldehyde, ethylene, PM 2.5 (particulate matter 2.5, e.g., suspended particulates smaller than 2.5 μm in aerodynamic diameter), and/or other suitable components in the air.

In one embodiment, an individual air quality index (IAQI) is determined by a level (e.g., concentration) of an individual air component. An air quality index (AQI) can be the highest of IAQI score(s) of those air components listed above. Each air component can be measured differently. For example, IAQI of PM 2.5 can be determined by an average concentration over 24 hours of the suspended particulates that are smaller than 2.5 μm. An IAQI of each of SO2, NO2, O3, and CO can be determined by an average concentration over one hour. The scale for IAQI of each air component is non-linear, as is the AQI score. Thus, an AQI of 100 does not mean twice the pollution of an AQI at 50, nor does it mean twice as harmful.

TABLE 1

| IAQI | $SO_2$ Avg./ 24 hr $\mu g/m^3$ | $SO_2$ Avg./hr $\mu g/m^3$ | $NO_2$ Avg./ 24 hr $\mu g/m^3$ | $NO_2$ Avg./ hr $\mu g/m^3$ | PM10 Avg./ 24 hr $\mu g/m^3$ |
|---|---|---|---|---|---|
| 0 | 0 | 0 | 0 | 0 | 0 |
| 50 | 50 | 150 | 40 | 100 | 50 |
| 100 | 150 | 500 | 80 | 200 | 150 |
| 150 | 475 | 650 | 180 | 700 | 250 |
| 200 | 800 | 800 | 280 | 1200 | 350 |
| 300 | 1600 | — | 565 | 2340 | 420 |

| IAQI | CO Avg./ 24 hr $mg/m^3$ | CO Avg./ hr $mg/m^3$ | $O_3$ Avg./ hr $\mu g/m^3$ | $O_3$ Avg./ 8 hr $\mu g/m^3$ | PM2.5 Avg./ 24 hr $\mu g/m^3$ |
|---|---|---|---|---|---|
| 0 | 0 | 0 | 0 | 0 | 0 |
| 50 | 2 | 5 | 160 | 100 | 35 |
| 100 | 4 | 10 | 200 | 160 | 75 |
| 150 | 14 | 35 | 300 | 215 | 115 |
| 200 | 24 | 60 | 400 | 265 | 150 |
| 300 | 36 | 90 | 800 | 800 | 250 |

Table 1 lists IAQI levels for exemplary air components. For example, in Table 1, an IAQI level between 0-50 indicates excellent air quality; an IAQI level between 50-100 indicates good air quality; an IAQI level between 101-150 indicates lightly polluted air quality; an IAQI level between 151-200 indicates moderately polluted air quality; an IAQI level between 201-300 indicates heavily polluted air quality; and an IAQI level higher than 300 indicates severely polluted air quality. Based on Table 1, air quality can be determined using the disclosed LED lighting device having an air quality detection function.

In one embodiment, when AQI is greater than 50, the air component(s) having highest IAQI are primary pollutant(s). For PM 2.5 measurements, AQI can be 500, when the suspended particulates smaller than 2.5 μm have an average concentration over 24 hours of about 500 $\mu m/m^3$ or greater in the air.

Figure 5:
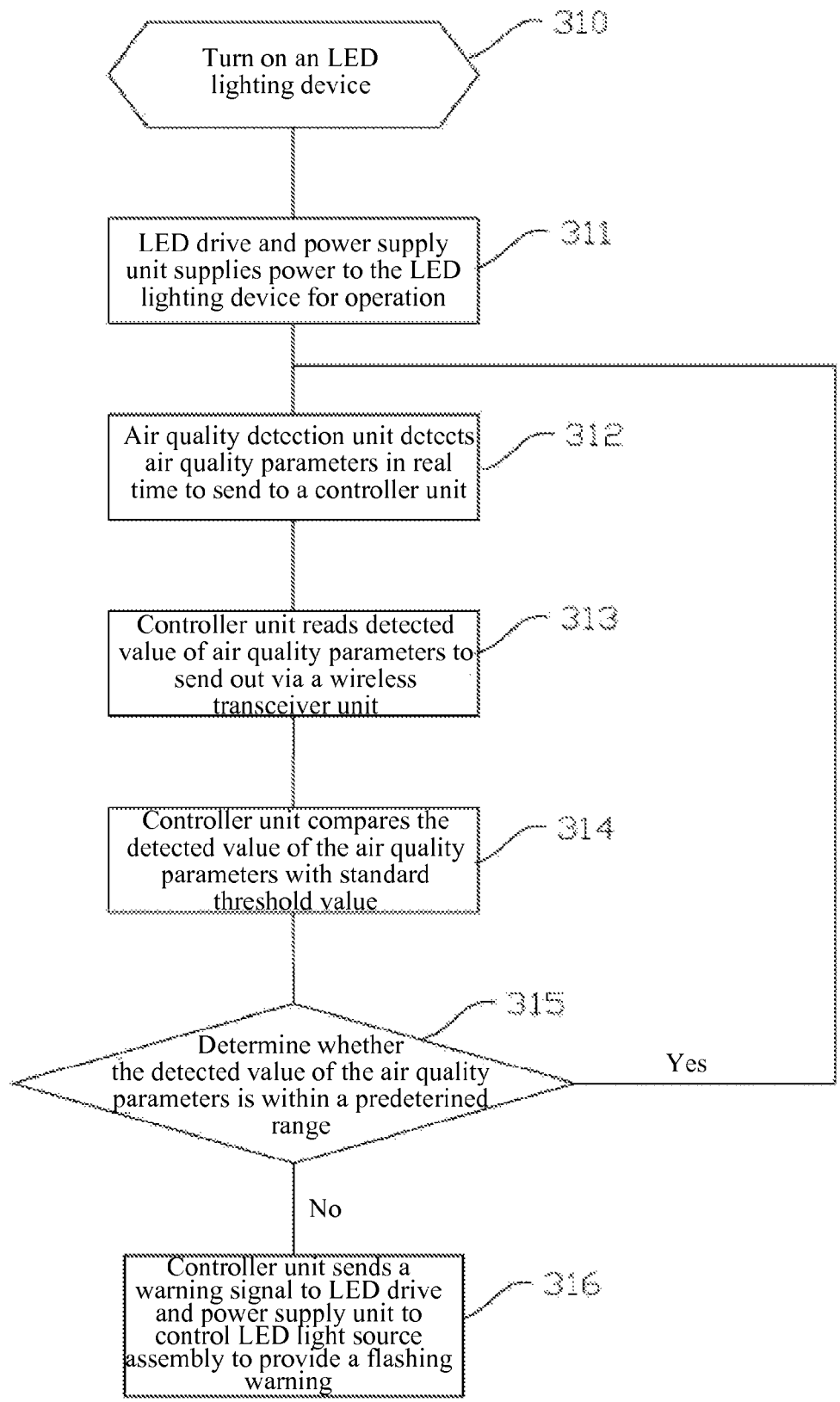
FIG. 5 depicts an exemplary method for detecting air quality using an LED lighting device consistent with various disclosed embodiments.

FIG. 5 depicts an exemplary method for detecting air quality using the disclosed LED lighting device, e.g., as shown in FIGS. 1-4 in accordance with various disclosed embodiments.

In Step 310, an exemplary LED lighting device can be turned on.

In Step 311, an LED drive and power supply unit 11 can supply power to operate the LED lighting device 1.

In Step 312, an air quality detection unit 13 can detect air quality parameters in real-time and send the detected value to the controller unit 12.

In Step 313, the controller unit 12 can read and process detected value of the air quality parameters, which are sent out, e.g., to a smart terminal, via the wireless transceiver unit 15.

In Step 314, the controller unit 12 can compare the detected value of the air quality parameters with a standard threshold value.

In Step 315, it is determined whether the detected value of the air quality parameters is within a predetermined range. In some cases, the predetermined range can be considered as "a safe range".

In Step 316, when the detected value of the air quality parameters does not exceed the predetermined range, the method then returns to perform Step 312 to continue monitoring and detecting air quality parameters in real-time. When the detected value of the air quality parameters exceeds the predetermined range, the controller unit 12 can send a warning signal to the LED drive and power supply unit 11 such that the LED drive and power supply unit 11 controls the LED light source assembly 14 to provide a flashing warning light.

Figure 6:
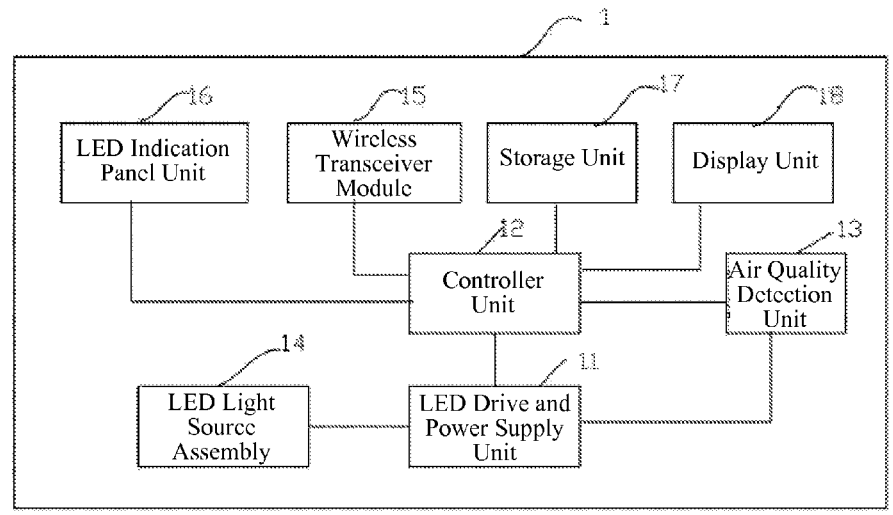
FIG. 6 depicts another exemplary LED lighting device consistent with various disclosed embodiments.

In another example, as shown in FIG. 6, an exemplary LED lighting device can be similar to the exemplary LED lighting device of FIG. 1 except that: the exemplary LED lighting device of FIG. 6 can further include an LED indication panel unit 16, a storage unit 17, and/or a display unit 18.

The LED indication panel unit 16 can include a number of light-emitting diodes that can be differently-colored. The LED indication panel unit 16 can be connected to the controller unit 12. The controller unit 12 can control the differently-colored LEDs in LED indication panel unit 16 to provide a warning signal based on the detected air quality.

The storage unit 17 can support pluggable SD cards. The storage unit 17 can be connected to the controller unit 12. The storage unit 17 can be used to store a detected date, according to a setting of a starting date and an ending date, to collect a name of specific sensitive gas in the air and to collect air quality index (AQI).

The display unit 18 can be one or more of an LED digital tube, LCD, OLED, and/or any other suitable display device. The display unit 18 can be connected to the controller unit 12 and configured to display in real-time the air quality factor corresponding to air quality parameter(s) and to display in real-time information including the air quality factor for users to query back, e.g., by using a smart terminal.

In various embodiments, the LED lighting device can be integrated as one single device. For example, each component (e.g., as shown in FIGS. 1-4 and 6) of the disclosed LED lighting device can be integrated together in the lamp body of the device. In one embodiment, to ensure RF transceiver functions as the wireless transceiver module as desired, an embedded antenna can be included in the integrated LED lighting device. The embedded antenna can also be configured to fit a shape of the lamp body of the LED lighting device without increasing size of the resultant device and to maintain the design of the resultant device. In various embodiments, the wireless transceiver modules may be configured with automatic frequency hopping functions to avoid interference with other radio devices.

The embodiments disclosed herein are exemplary only. Other applications, advantages, alternations, modifications, or equivalents to the disclosed embodiments are obvious to those skilled in the art and are intended to be encompassed within the scope of the present disclosure.

INDUSTRIAL APPLICABILITY AND ADVANTAGEOUS EFFECTS

Without limiting the scope of any claim and/or the specification, examples of industrial applicability and certain advantageous effects of the disclosed embodiments are listed for illustrative purposes. Various alternations, modifications, or equivalents to the technical solutions of the disclosed embodiments can be obvious to those skilled in the art and can be included in this disclosure.

Figure 7:
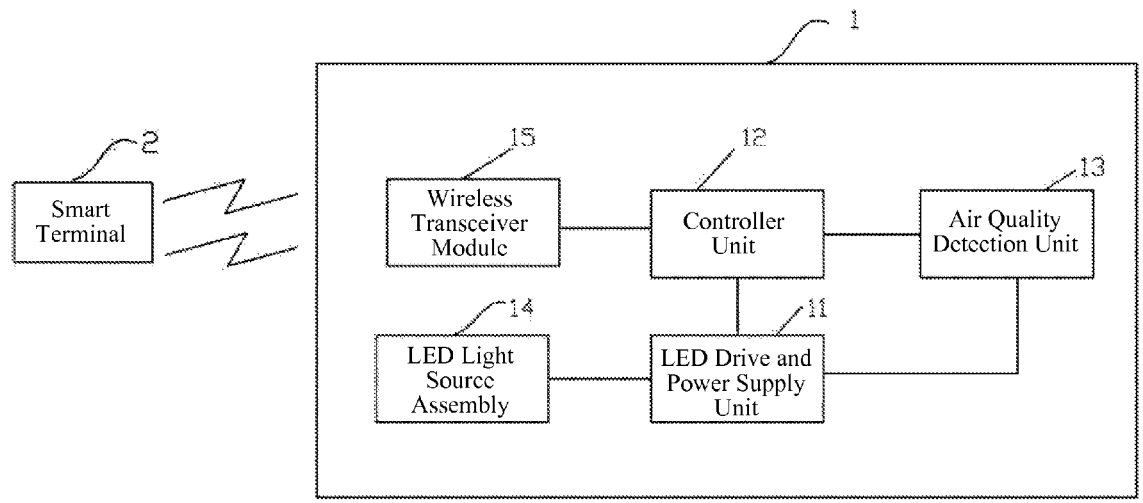
FIG. 7 depicts an exemplary LED lighting system consistent with various disclosed embodiments.
Figure 8:
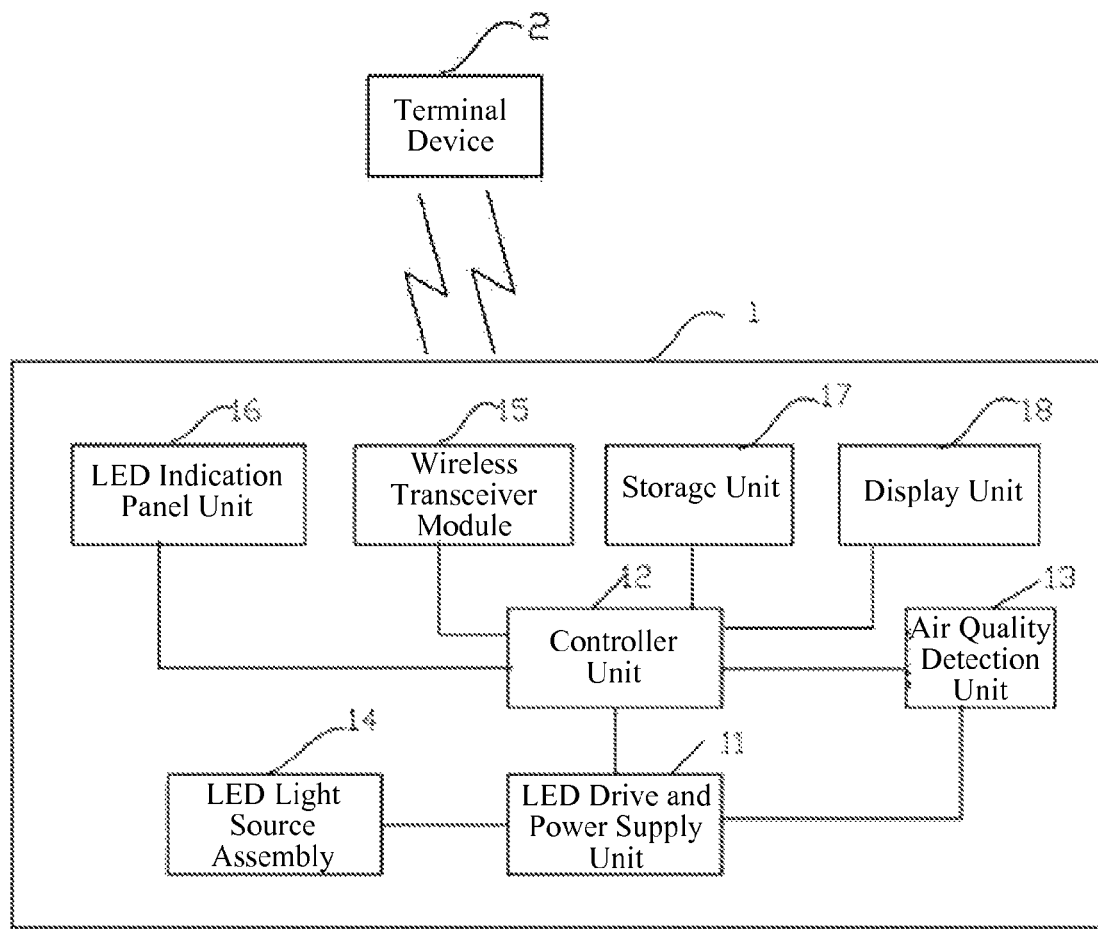
FIG. 8 depicts another exemplary LED lighting system consistent with various disclosed embodiments.

FIGS. 7-8 depict various exemplary LED lighting systems consistent with various disclosed embodiments. The exemplary LED lighting system can include a smart terminal 2 and one or more LED lighting devices 1 (e.g., as shown in FIGS. 1-4 and 6), configured to communicate with the smart terminal 2 via the wireless transceiver unit 15 in each LED lighting device 1.

For example, the wireless transceiver unit 15 can be connected to the controller unit 12 in a same LED lighting device 1. The wireless transceiver unit 15 can be configured to transmit data corresponding to the air quality parameter(s) to the smart terminal 2. In some cases, the wireless transceiver unit 15 can support a frequency band including 2.4 GHz, 5.2 GHz, 5.8 GHz, a combination thereof. The wireless transceiver unit 15 can support a bi-directional transmission.

Figure 9:
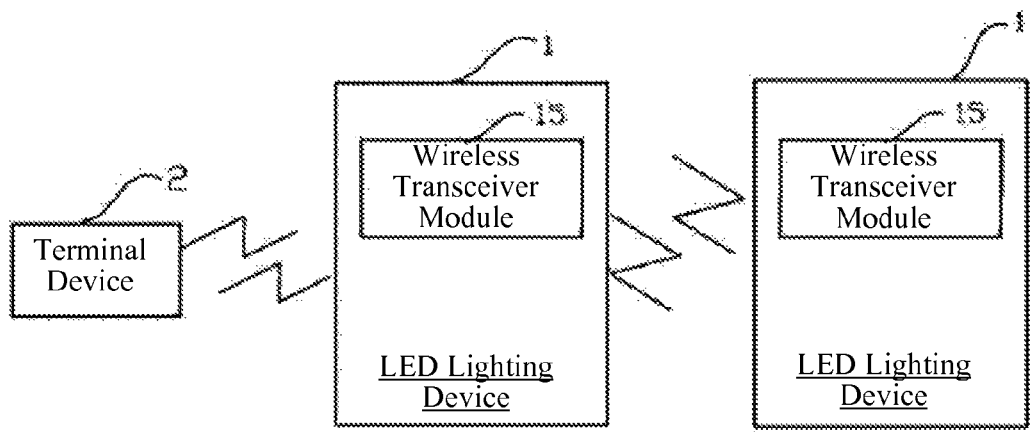
FIG. 9 depicts another exemplary LED lighting system consistent with various disclosed embodiments.

In various embodiments, the smart terminal 2 can remotely control the LED lighting device(s), which can be arranged to form a network such as a star and/or mesh type-network. By such networks, wireless signals can be transmitted between one another, and transmission range can be enlarged. For example, as shown in FIG. 9, an exemplary LED lighting system can include at least two LED lighting device nodes with each node including one LED lighting device. The LED lighting device nodes can be configured a mesh-shaped network or a star-shaped network controlled by the smart terminal 2. For example, each node is configured to transmit a wireless signal corresponding to the at least one air quality parameter from the wireless transceiver unit 15 of one of the LED lighting device nodes to other LED lighting device nodes covered by other wireless signals.

Based on the control of the smart terminal, each LED lighting device may be used to accommodate various detection needs. For example, each LED lighting device may detect air quality parameters of specific and different gas (and/or particles) according to the requirements of surrounding environment. Detected data from various different LED lighting devices can be transmitted to a same or different smart terminal for analysis and statistic studies. In some cases, the detected data from various different LED lighting devices can be correlated or otherwise connected with one another to provide an air quality monitoring of related regions.

The smart terminal 2 can include a mobile phone, a tablet PC, a desktop computer, a notebook, and/or any suitable terminal devices. The disclosed LED lighting system can access Internet or LAN for data transmission. In one embodiment, the smart terminal 2 can perform analysis and statistics to the data received from the wireless transceiver module 15 in each LED lighting device 1 to provide real-time information (or any related information) of the air quality of the region where a corresponding LED lighting device is located.

As disclosed, by combining an air quality detection unit with an LED lighting device that are widely distributed and widely installed, the disclosed LED lighting devices/systems/methods can thus provide real-time and convenient air quality monitoring. This can be beneficial to environmental protection.

REFERENCE SIGN LIST

LED lighting device 1
Smart Terminal 2
LED drive and power supply unit 11
Controller unit 12
Air quality detection unit 13
LED light source assembly 14
Wireless transceiver unit 15
Analog circuit 13a
Analog sensor 130
Signal processing circuit 131
ADC circuit 132

Digital sensor 13*b*
LED indication panel unit 16
Storage unit 17
Display unit 18

What is claimed is:

1. An LED (light emitting diode) lighting device having an air quality detection function, comprising:
at least one air quality detection unit, configured to detect at least one air quality parameter;
at least one controller unit connected to the air quality detection unit to process data corresponding to the at least one air quality parameter detected and collected by the at least one air quality detection unit;
at least one LED light source assembly controlled by the at least one controller unit, configured to function as a general lighting source for a space, and further configured as an alarm unit for receiving the data corresponding to the at least one air quality parameter from the at least one controller unit and for providing a flashing warning light when the detected value of the air quality parameters exceeds a predetermined range;
at least one LED driver and power supply unit connected to the at least one LED light source assembly to drive the at least one LED light source assembly, and to supply power to the entire LED lighting device;
a display unit connected to the at least one controller unit and configured to display in real-time an air quality factor corresponding to the at least one air quality parameter and to display information including the air quality factor for users to query back, wherein the display unit comprises an LCD, an OLED, or a combination thereof; and
a lamp body, wherein the at least one air quality detection unit, the at least one controller unit, the at least one LED light source assembly, the at least one LED driver and power supply unit and the display unit are integrated together in the lamp body.

2. The device according to claim 1, wherein the air quality detection unit comprises an analog circuit, the analog circuit comprising:
an analog sensor, configured to convert a non-electrical signal corresponding to the at least one air quality parameter into an analog signal and then to output the analog signal;
a signal processing circuit connected to the analog sensor to scale, filter, and amplify the analog signal from the analog sensor and to further output a processed analog signal; and
an ADC circuit configured: to receive the processed analog signal from the signal processing circuit, to convert the processed analog signal into a digital signal, and to output the digital signal to the at least one controller unit for conversion, calculation, and storage of the digital signal.

3. The device according to claim 1, wherein the air quality detection unit is a digital sensor directly connected to the at least one controller unit to provide a digital signal corresponding to the at least one air quality parameter, and wherein the at least one controller unit is configured to read, convert, calculate, and store the digital signal according to a bus protocol.

4. The device according to claim 1, wherein the air quality detection unit comprises at least one analog circuit and at least one digital sensor,
wherein the at least one analog circuit comprises:
an analog sensor, configured to convert a non-electrical signal corresponding to the at least one air quality parameter into an analog signal and then to output the analog signal,
a signal processing circuit connected to the analog sensor to scale, filter, and amplify the analog signal from the analog sensor and to further output a processed analog signal, and
an ADC circuit configured: to receive the processed analog signal from the signal processing circuit, to convert the processed analog signal into a digital signal, and to output the digital signal to the at least one controller unit for conversion, calculation, and storage of the digital signal, and
wherein the at least one digital sensor is directly connected to the at least one controller unit to provide a digital signal corresponding to the at least one air quality parameter, and wherein the at least one controller unit is configured to read, convert, calculate, and store the digital signal according to a bus protocol.

5. The device according to claim 1, wherein the at least one air quality parameter comprises a concentration of one or more of carbon monoxide, methanol, ethanol, formaldehyde, isopropanol, acetaldehyde, SO2, H2, H2S, phenol, formaldehyde, ethylene, and PM 2.5 (particulate matter 2.5), in the air.

6. The device according to claim 1, further comprising an LED indication panel unit connected to the at least one controller unit, the LED indication panel unit comprising a plurality of light emitting diodes with different colors to indicate different air qualities corresponding to the at least one air quality parameter.

7. The device according to claim 1, further comprising a storage unit connected to the at least one controller unit and configured to support a pluggable SD card, wherein the storage unit is further configured to store the data corresponding to the at least one air quality parameter in real-time according to a setting of a starting date and an ending date.

8. The device according to claim 1, further comprising a wireless transceiver unit connected to the at least one controller unit and configured to transmit the data corresponding to the at least one air quality parameter to a smart terminal.

9. An LED lighting system having an air quality detection function, comprising:
one or more LED lighting devices and at least one smart terminal, wherein each of the one or more LED lighting devices comprises:
at least one air quality detection unit configured to detect at least one air quality parameter;
at least one controller unit connected to the air quality detection unit to process data corresponding to the at least one air quality parameter detected and collected by the at least one air quality detection unit;
at least one LED light source assembly controlled by the at least one controller unit, configured to function as a general lighting source for a space, and further configured as an alarm unit for receiving the data corresponding to the at least one air quality parameter from the at least one controller unit and for providing a flashing warning light when the detected value of the air quality parameters exceeds a predetermined range;
at least one LED driver and power supply unit connected to the at least one LED light source assembly to drive the at least one LED light source assembly, and to supply power to the entire LED lighting device;
at least one wireless transceiver unit connected to the at least one controller unit and configured to transmit the data corresponding to the at least one air quality parameter to the at least one smart terminal;

a display unit connected to the at least one controller unit and configured to display in real-time an air quality factor corresponding to the at least one air quality parameter and to display information including the air quality factor for users to query back, wherein the display unit comprises an LCD, an OLED, or a combination thereof; and a lamp body, wherein the at least one air quality detection unit, the at least one controller unit, the at least one LED light source assembly, the at least one LED driver and power supply unit and the display unit are integrated together in the lamp body.

10. The system according to claim 9, wherein the wireless transceiver unit is supported by one or more of zigbee, WiFi, and bluetooth.

11. The system according to claim 9, wherein the smart terminal comprises a mobile phone, a tablet PC, a desktop computer, and a notebook.

12. The system according to claim 9, further comprising at least two LED lighting device nodes with each node including one LED lighting device, wherein each node is configured to transmit a wireless signal corresponding to the at least one air quality parameter from the at least one wireless transceiver unit to other different nodes covered by other wireless signals correspondingly.

13. The system according to claim 12, wherein
the LED lighting device nodes are configured as a mesh-shaped network or star-shaped network controlled by the at least one smart terminal;
each LED lighting device node is configured to detect an air quality parameter of a specific and different gas or particles according to requirements of surrounding environment, and to transmit the detected air quality parameter to the at least one smart terminal; and
the detected air quality parameters from the at least two LED lighting device nodes are correlated to provide an air quality monitoring of related regions.

14. The system according to claim 9, further comprising:
a second air quality detection unit configured to detect at least one air quality parameter, wherein the second air quality detection unit is also integrated in the lamp body.

15. A method for detecting an air quality using an LED lighting device, comprising:

(a) providing an LED lighting device comprising an air quality detection unit, a controller unit, an LED light source assembly, an LED driver and power supply unit, a display unit and a wireless transceiver unit, wherein the LED light source assembly functions as a general lighting source for a space;

(b) detecting air quality parameters in real-time to provide a detected value by the air quality detection unit, wherein the air quality detection unit sends the detected value to the controller unit;

(c) obtaining the detected value of the air quality parameters by the controller unit, wherein the detected value is sent out to a smart terminal via the wireless transceiver unit;

(d) comparing the detected value of the air quality parameters with a standard threshold value by the controller unit;

(e) determining whether the detected value of the air quality parameters is within a predetermined range;

(f) displaying in real-time an air quality factor corresponding to the air quality parameters and displaying information including the air quality factor for users to query back, wherein the display unit comprises an LCD, an OLED, or a combination thereof;

(g) repeating steps (b)-(f), when the detected value of the air quality parameters is within the predetermined range; and (h) sending a warning signal by the controller unit to the LED drive and power supply unit such that the LED drive and power supply unit controls the LED light source assembly to provide a flashing warning light, when the detected value of the air quality parameters exceeds the predetermined range;

wherein the LED lighting device further comprises a lamp body, and the air quality detection unit, the controller unit, the LED light source assembly, the LED driver and power supply unit, the display unit and the wireless transceiver unit are integrated together in the lamp body.

16. The method according to claim 15, wherein each of the air quality parameters comprises a concentration of one or more of carbon monoxide, methanol, ethanol, formaldehyde, isopropanol, acetaldehyde, SO2, H2, H2S, phenol, formaldehyde, ethylene, and PM 2.5 (particulate matter 2.5), in the air.

* * * * *